HACKBERRY TREE
Filed Nov. 3, 1966 2 Sheets-Sheet 1
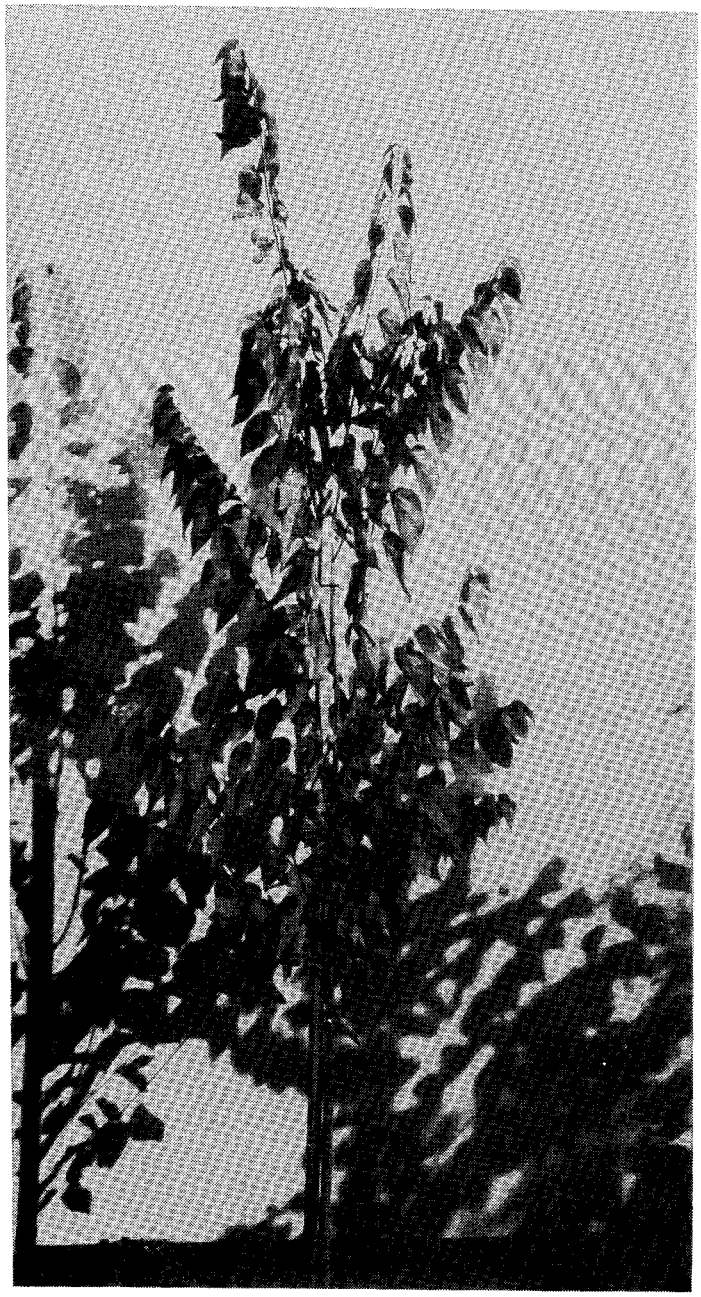
Inventor.
William Flemer, III
By: Robb & Robb
Attorneys.

Feb. 6, 1968 W. FLEMER III Plant Pat. 2,795
HACKBERRY TREE
Filed Nov. 3, 1966 2 Sheets-Sheet 2
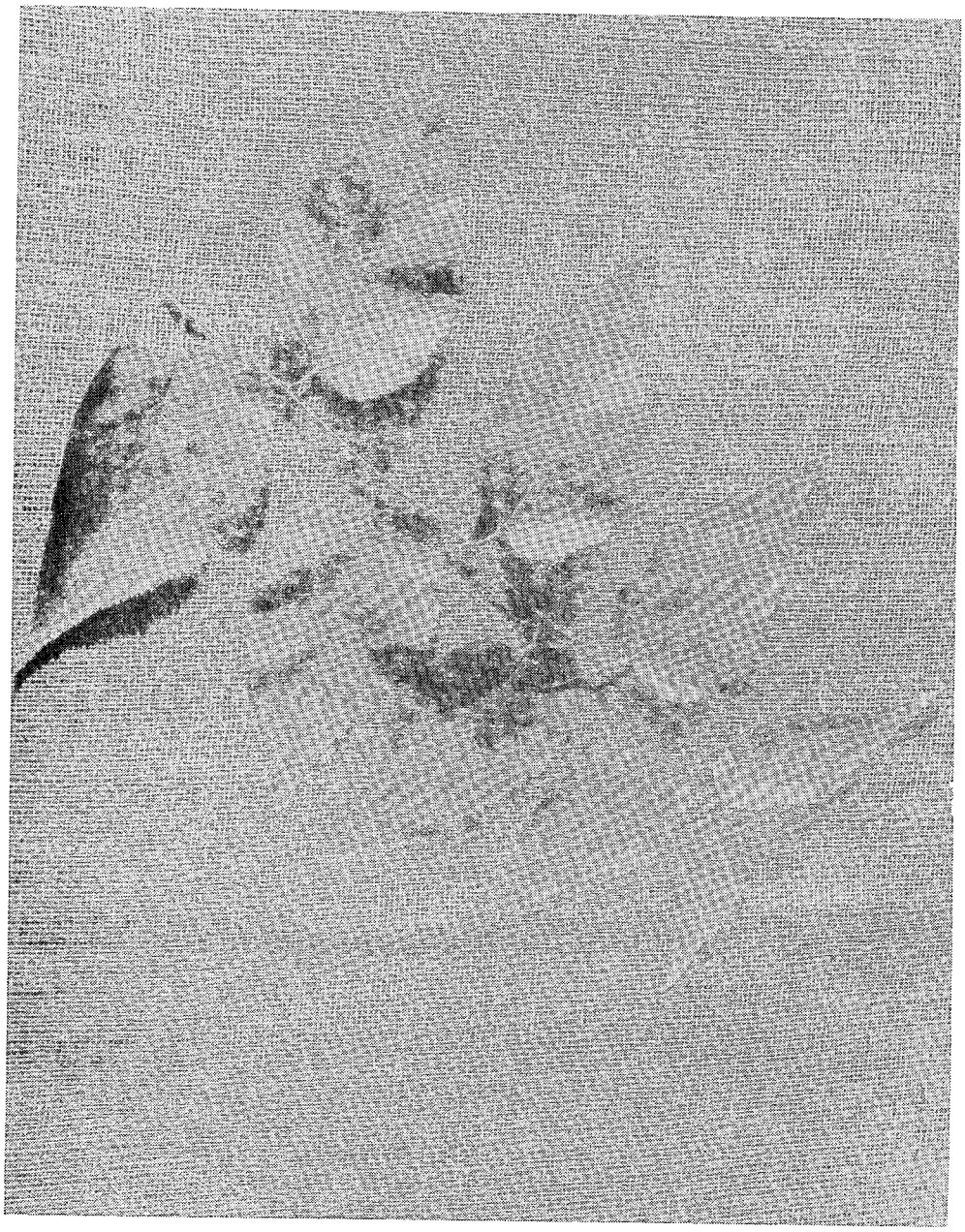
Inventor.
William Flemer, III
By: Robb & Robb
Attorneys.

United States Patent Office

Plant Pat. 2,795
Patented Feb. 6, 1968

2,795
HACKBERRY TREE

William Flemer III, Princeton, N.J., assignor to Treesearch, Kingston, N.J., a partnership composed of William Flemer III, John W. Flemer, and Richard J. Henkel Filed Nov. 3, 1966, Ser. No. 591,935
1 Claim. (Cl. Plt.—51)

The present invention relates to a new and distinct variety of hackberry tree (botanically known as Celtis), which was originated by me by crossing an unnamed and un-patented variety of the species botanically known as *Celtis occidentalis* with another unnamed and unpatented variety of the species botanically known as *Celtis laevigata*.

As the result of this breeding, I have produced a new and improved variety of hackberry tree which is distinguished from its parents, as well as from all other varieties of which I am aware, as evidenced by the following unique combination of characteristics which are outstanding therein:

(1) A very vigorous and rapid habit of growth, equal to from 3 to 4 times more rapid than *Celtis occidentalis* seedlings grown in the same rows under identical conditions;

(2) Large dark green foliage which is resistant to defoliation and leaf scorch under summer heat conditions, with the leaves being retained unblemished when *Celtis occidentalis* seedlings in the same rows become almost completely defoliated under the same conditions; and (3) Good resistance to "Witches Broom" twig disease.

Asexual reproduction of my new variety by budding or bud-grafting, as performed by me in Plainsboro Township, N.J., shows that the foregoing characteristics and distinctions come true and are established and transmitted through succeeding propagations.

The accompanying drawings show a typical specimen tree of my new variety of hackberry tree, as well as typical foliage specimens as depicted on an enlarged scale.

The following is a detailed description of my new variety, with color terminology in accordance with the Nickerson Color Fan, published by Munsell Color Company, Inc., of Baltimore, Md., except where general color terms of ordinary dictionary significance are obvious, as based on specimens grown and observed in Plainsboro Township, N.J.:

Parentage: Seedling.
*Seed parent.*—An unnamed variety of *Celtis occidentals.*
*Pollen parent.*—An unnamed variety of *Celtis laevigata.*

Tree: Large size; tall; spreading; with deliquescent branching habit.
*Trunk.*—Slender; rough; moderately corky.
*Branches.*—Slender; puberulous. Color—Grayish-Olive Green, Plate 2.5GY 3/1.

Foliage:
*Leaves.*—Abundant; from 7 to 9 pairs of prominent veins. Length—average 20 cm. Width—average 10 cm. Shape—ovate; acuminate; with oblique bases; densely hirsute on both upper and lower surfaces. Color: upper surface—Moderate Yellow-Green, Plate 2.5GY 5/5; lower surface—Dark Green, Plate 5G 3/4. Margin—serrate; depth of teeth—0.2 cm.; width of teeth—0.5 cm. Petiole—short (about 1.5 cm. long). Stipules—none.

Flower buds: None.
Flowers: None.
Fruit: None.

I claim:

1. A new and distinct variety of hackberry tree (Celtis), substantially as herein shown and described, characterized particularly as to novelty by the unique combination of a very vigorous and rapid habit of growth, equal to 3 to 4 times more rapid than *Celtis occidentalis* seedlings grown in the same rows under identical conditions, large dark green foliage which is resistant to defoliation and leaf scorch under summer heat conditions, with the leaves being retained unblemished when *Celtis occidentalis* seedlings in the same rows become almost completely defoliated under the same conditions and good resistance to "Witches Broom" twig disease.

No references cited.

ROBERT E. BAGWILL, *Primary Examiner.*